(12) United States Patent
Ashton et al.

(10) Patent No.: US 10,265,025 B2
(45) Date of Patent: Apr. 23, 2019

(54) ELECTROCARDIOGRAM NOISE REDUCTION

(71) Applicant: BIOSENSE WEBSTER (ISRAEL), LTD., Yokneam (IL)

(72) Inventors: John Hardy Ashton, Glendora, CA (US); George Kamin, Arcadia, CA (US); Jose G. Ramos, Paramount, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 1229 days.

(21) Appl. No.: 13/926,277

(22) Filed: Jun. 25, 2013

(65) Prior Publication Data

US 2014/0378805 A1    Dec. 25, 2014

(51) Int. Cl.
*A61B 18/04* (2006.01)
*A61B 5/04* (2006.01)
(Continued)

(52) U.S. Cl.
CPC ............ *A61B 5/7217* (2013.01); *A61B 5/042* (2013.01); *A61B 5/04012* (2013.01);
(Continued)

(58) Field of Classification Search
CPC ...... A61N 1/08; A61N 2001/086; A61N 1/05; A61N 1/36125; A61B 18/1492;
(Continued)

(56) References Cited

U.S. PATENT DOCUMENTS 3,774,106 A * 11/1973 MacPhee ............. G01R 31/024
                                                       324/510
4,644,960 A *  2/1987 Johans ................... A61B 5/042
                                                       604/20
(Continued)

FOREIGN PATENT DOCUMENTS

CN    102596281 A    7/2012
CN    103156683 A    6/2013
(Continued)

OTHER PUBLICATIONS

European Search Report dated Dec. 3, 2014 from corresponding European Patent Application No. 14173937.5.
(Continued)

*Primary Examiner* — Ronald Hupczey, Jr.
*Assistant Examiner* — Brian M Antiskay
(74) *Attorney, Agent, or Firm* — Roberts Mlotkowski Safran Cole & Calderon, P.C.

(57) ABSTRACT

Methods and systems of catheterization include a flexible catheter adapted for insertion into a heart of a living subject. The catheter has a lumen for passing an electrically conductive fluid therethrough, which is propelled by a peristaltic pump. A fluid reservoir connected to the lumen supplies the fluid to the catheter. Electrocardiogram circuitry is connectable to the subject for monitoring electrical activity in the heart. An electrically conductive cable diverts induced charges in the fluid from the catheter electrodes, for example by shorting to a rotating element in the peristaltic pump.

26 Claims, 8 Drawing Sheets

(51) Int. Cl.
*A61N 1/00* (2006.01)
*A61B 5/00* (2006.01)
*A61B 5/042* (2006.01)
*A61B 18/14* (2006.01)
*A61B 18/00* (2006.01)

(52) U.S. Cl.
CPC . *A61B 18/1492* (2013.01); *A61B 2018/00011* (2013.01); *A61B 2018/00351* (2013.01); *A61B 2018/00577* (2013.01); *A61B 2018/00839* (2013.01); *A61M 2205/0233* (2013.01)

(58) Field of Classification Search
CPC ........ A61B 2018/00577; A61B 5/0422; A61B 18/24; A61B 2562/164; A61B 5/6852; A61B 5/7217; A61B 2562/182
USPC ................ 600/372–374, 377, 381, 508–509; 606/20–26
See application file for complete search history.

(56) References Cited

U.S. PATENT DOCUMENTS

| | | | |
|---|---|---|---|
| 4,790,311 A * | 12/1988 | Ruiz | A61B 18/082 606/28 |
| 5,127,907 A | 7/1992 | Coutre | |
| 5,387,088 A * | 2/1995 | Knapp | F04B 43/1253 417/477.1 |
| 6,226,542 B1 | 5/2001 | Reisfeld | |
| 6,301,496 B1 | 10/2001 | Reisfeld | |
| 6,814,733 B2 | 11/2004 | Schwartz | |
| 6,870,109 B1 | 3/2005 | Villarreal | |
| 6,892,091 B1 | 5/2005 | Ben Haim | |
| 6,997,924 B2 | 2/2006 | Schwartz | |
| 7,092,750 B2 | 8/2006 | Van Ess | |
| 7,156,816 B2 | 1/2007 | Schwartz | |
| 7,536,218 B2 | 5/2009 | Govari | |
| 7,756,576 B2 | 7/2010 | Levin | |
| 7,785,284 B2 | 8/2010 | Baraldi | |
| 7,853,324 B2 | 12/2010 | Stevenson | |
| 7,885,700 B2 | 2/2011 | Clark | |
| 8,108,039 B2 | 1/2012 | Saliga | |
| 8,116,862 B2 | 2/2012 | Stevenson | |
| 8,301,243 B2 | 10/2012 | Stevenson | |
| 8,311,628 B2 | 11/2012 | Stevenson | |
| 2002/0177765 A1* | 11/2002 | Bowe | A61B 18/1492 600/374 |
| 2004/0108206 A1 | 6/2004 | Bhullar et al. | |
| 2006/0106303 A1* | 5/2006 | Karmarkar | A61M 25/00 600/422 |
| 2006/0186010 A1* | 8/2006 | Warnack | A61M 25/002 206/438 |
| 2009/0162228 A1* | 6/2009 | Nelson | F04B 43/1253 417/477.2 |
| 2009/0280016 A1* | 11/2009 | Carroll | F04B 43/1253 417/477.3 |
| 2010/0222859 A1* | 9/2010 | Govari | A61B 5/0422 607/119 |
| 2010/0331658 A1* | 12/2010 | Kim | A61B 18/18 600/373 |
| 2012/0035616 A1* | 2/2012 | Olsen | A61N 1/05 606/129 |
| 2012/0046562 A1* | 2/2012 | Powers | A61B 5/042 600/509 |
| 2012/0165735 A1 | 6/2012 | Keh | |
| 2012/0282126 A1 | 11/2012 | Brandt et al. | |
| 2013/0172873 A1 | 7/2013 | Govari et al. | |

FOREIGN PATENT DOCUMENTS

| | | |
|---|---|---|
| EP | 2 604 211 A1 | 6/2013 |
| JP | 2001087392 A | 4/2001 |
| JP | 2006526447 A | 11/2006 |
| JP | 2010502408 A | 1/2010 |
| JP | 2011224373 A | 11/2011 |
| JP | 2013509899 A | 3/2013 |
| WO | WO 2004/108206 A1 | 12/2004 |
| WO | WO 2009/044220 A1 | 4/2009 |

OTHER PUBLICATIONS

Metz, Samuel, "ECG artifacts during cardiopulmonary bypass—an alternative method", Anesthesia-Analgesia, Jan. 1, 1991, pp. 715-716.

Patel, Santosh I. et al., "Equipment-related Electrocardiographic Artifacts", Anesthesiology, Jan. 1, 2008, pp. 138-148, vol. 108, No. 1.

Pending U.S. Appl. No. 13/339,782, filed Dec. 29, 2011.

* cited by examiner

ELECTROCARDIOGRAM NOISE REDUCTION

BACKGROUND OF THE INVENTION

Field of the Invention

This invention relates to medical catheterization. More particularly, this invention relates to electrocardiographic monitoring during medical catheterization procedures.

Description of the Related Art

The meanings of certain acronyms and abbreviations used herein are given in Table 1.

TABLE 1

Acronyms and Abbreviations

| | |
|---|---|
| ECG | Electrocardiogram |
| PIU | Patient Interface Unit |
| RF | Radiofrequency |

Medical catheterizations are routinely carried out today. For example, in cases of cardiac arrhythmias, such as atrial fibrillation, which occur when regions of cardiac tissue abnormally conduct electric signals. Procedures for treating arrhythmia include surgically disrupting the origin of the signals causing the arrhythmia, as well as disrupting the conducting pathway for such signals. By selectively ablating cardiac tissue by application of energy, e.g., radiofrequency energy via a catheter, it is sometimes possible to cease or modify the propagation of unwanted electrical signals from one portion of the heart to another. The ablation process destroys the unwanted electrical pathways by formation of non-conducting lesions.

A known difficulty in the use of radiofrequency energy for cardiac tissue ablation is controlling local heating of tissue. There are tradeoffs between the desire to create a sufficiently large lesion to effectively ablate an abnormal tissue focus, or block an aberrant conduction pattern, and the undesirable effects of excessive local heating. If the radiofrequency device creates too small a lesion, then the medical procedure could be less effective, or could require too much time. On the other hand, if tissues are heated excessively then there could be local charring effects due to overheating. Such overheated areas can develop high impedance, and may form a functional barrier to the passage of heat. The use of slower heating provides better control of the ablation, but unduly prolongs the procedure. Commonly assigned application Ser. No. 13/339,782, which is herein incorporated by reference, discloses the use of an irrigation pump to cause irrigation fluid to flow through a lumen of the catheter in order to cool the ablation site.

SUMMARY OF THE INVENTION

There is provided according to embodiments of the invention a catheterization system, which avoids spurious electrical interference in electrical monitoring circuitry when a peristaltic pump is operating to irrigate an ablation site. The system includes a flexible catheter adapted for insertion into a heart of a living subject. The catheter has a lumen for passing an electrically conductive fluid therethrough to exit the catheter at its distal portion, the lumen connectable to an irrigation pump to form a fluid communication therewith. A fluid reservoir is connected to the lumen for supplying the electrically conductive fluid to the catheter. Electrocardiogram circuitry is connectable to the subject for monitoring electrical activity in the heart. An electrically conductive cable links the electrically conductive fluid to an electrode that is in contact with the subject.

According to an aspect of the system, the catheter has mapping electrodes disposed on the distal portion and the electrode is located on the catheter proximal to the mapping electrodes.

According to a further aspect of the system, the electrode is located on a second catheter that is introduced into the subject.

According to one aspect of the system, the catheter has an inlet port, and a connector electrically contacts the electrically conductive fluid at the inlet port, and connects the electrically conductive fluid to a patient ground.

According to another aspect of the system, the electrically conductive cable is electrically connected to the electrically conductive fluid downstream of the irrigation pump.

According to an additional aspect of the system, the electrically conductive cable is a metallically shielded cable.

There is further provided according to embodiments of the invention a catheterization system, including a flexible catheter adapted for insertion into a heart of a living subject. The catheter has a lumen for passing an electrically conductive fluid therethrough to exit the catheter at its distal portion. A fluid reservoir is connected by a hydraulic line to the lumen for supplying the electrically conductive fluid to the catheter. The system includes a pump for propelling the electrically conductive fluid to the lumen of the catheter. The pump has a rotating element that acts upon the hydraulic line. An electrically conductive cable forms an electrical connection between the electrically conductive fluid in the hydraulic line and the rotating element.

According to an additional aspect of the system, the rotating element is metallic.

According to another aspect of the system, the rotating element is formed from a ceramic.

According to yet another aspect of the system, the rotating element is formed from a polymer.

According to still another aspect of the system, the rotating element is formed from an acetal homopolymer.

According to yet another aspect of the system, the electrically conductive cable connects to the frame of the pump.

According to still another aspect of the system, the electrically conductive cable connects to the rotating element of the pump.

According to an additional aspect of the system, the rotating element is electrically non-conductive.

According to one aspect of the system, the electrical connection with the electrically conductive fluid is downstream from the pump.

According to a further aspect of the system, the electrical connection with the electrically conductive fluid is upstream from the pump.

According to one aspect of the system, a portion of an outer surface of the hydraulic line is coated with an antistatic chemical, including the portion contacting the outer surface with the rotating element of the pump.

According to one aspect of the system, the contacting portion of an outer surface of the hydraulic line is coated with an antistatic chemical selected from the group consisting of soap water, saline and water.

According to a further aspect of the system, the contacting portion of an outer surface of the hydraulic line is coated with an electrical conductor.

There is further provided according to embodiments of the invention a method for monitoring electrical activity, which is carried out by connecting a reservoir of an electrically conductive fluid to a peristaltic pump having a rotating element, wherein the peristaltic pump exerts a force on a hydraulic line to cause the electrically conductive fluid to flow through the hydraulic line. The method is further carried out by connecting electrocardiogram circuitry to the subject, forming an electrical connection between the electrically conductive fluid and the peristaltic pump, and while operating the peristaltic pump, monitoring electrical activity in the heart with the electrocardiogram circuitry.

Yet another aspect of the method a portion of the hydraulic line is coated with an electrical conductor and the portion in contact with the rotating element.

According to still another aspect of the method, the electrical conductor is indium tin oxide.

According to an additional aspect of the method, the electrical conductor is aluminum foil.

In a further aspect of the method the outer surface of the contacting portion of the hydraulic line is coated with a material containing liquid water and an ionic surfactant.

An additional aspect of the method includes coating an outer surface of a portion of the hydraulic line with an anti-static chemical additive.

According to still another aspect of the method the contacting portion of the hydraulic line is impregnated with an anti-static chemical.

According to one aspect of the method a portion of an outer surface of the hydraulic line is coated with an anti-static chemical and includes the portion in contact with the rotating element.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as USB memory, hard drive, electronic media or CD-ROM. The code may be distributed on such media, or may be distributed to users from the memory or storage of one computer system over a network of some type to storage devices on other computer systems for use by users of such other systems.

Definitions

"Noise" is a disturbance, including a random and persistent disturbance that obscures or reduces the clarity of a signal.

System Description

Figure 1:
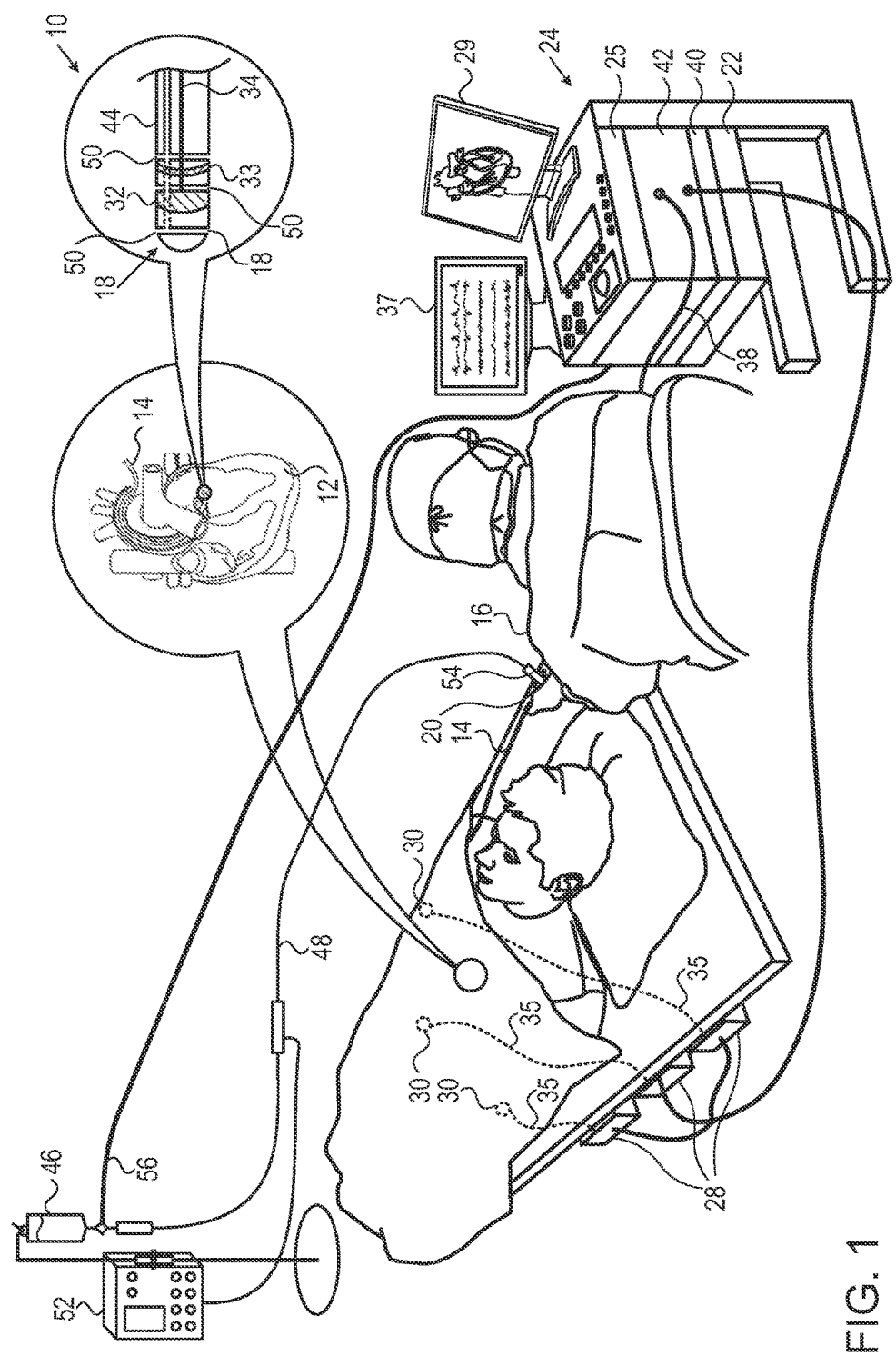
FIG. 1 is a pictorial illustration of a system for performing catheterization procedures on a heart of a living subject, which is constructed and operative in accordance with an embodiment of the invention.

Turning now to the drawings, reference is initially made to FIG. 1, which is a pictorial illustration of a system 10 for performing exemplary catheterization procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Electrical activation maps, anatomic positional information, i.e., of the distal portion of the catheter, and other functional images may then be prepared using a processor 22 located in a console 24, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765, which is capable of producing electroanatomic maps of the heart as required. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current from a radiofrequency (RF) generator 40 through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in the console 24.

Ablation energy and electrical signals can be conveyed to and from the heart 12 through the catheter tip and an ablation electrode 32 located at or near the distal tip 18 via cable 34 to the console 24. Pacing signals and other control signals may be also conveyed from the console 24 through the cable 34 and the ablation electrode 32 to the heart 12. Sensing electrodes 33, also connected to the console 24 are disposed between the ablation electrode 32 and the cable 34.

Wire connections 35 link the console 24 with body surface electrodes 30 and other components of a positioning sub-system. The electrode 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrode 32.

The console 24 typically contains one or more ablation power generators 25. The catheter 14 may be adapted to conduct ablative energy to the heart using radiofrequency energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures location and orientation coordinates of the catheter 14.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem may employ impedance measurement, as taught, for example in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. The processor 22 is typically a computer with appropriate signal processing circuits. The processor 22 is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received via cable 38 and used by the console 24 and the positioning system to compute the position and orientation of the catheter 14 and analyze the electrical signals from the electrodes, and generate desired electroanatomic maps.

The system 10 may include an electrocardiogram (ECG) monitor 37, coupled to receive signals from one or more body surface electrodes. The ECG signal is typically received through an interface with the console 24, e.g., a patient interface unit 42 having an analog input and an isolated ground may be used to provide an ECG synchronization signal to the console 24.

An electrically conductive fluid, e.g., saline, Ringer's lactate, is delivered through a lumen 44 in the catheter 14 from a reservoir 46 via a hydraulic line 48. The electrically conductive fluid is sometimes referred to herein as "saline" for convenience, it being understood that this is by way of example and not of limitation. The lumen 44 terminates in exit pores 50 through which the liquids emerge to cool the electrode 32 and the ablation site. A peristaltic pump 52 is connected to the hydraulic line 48 and causes the fluid to be delivered to the catheter 14 through an entrance port 54 at a desired rate. One difficulty with such an arrangement is that operation of equipment in the environment, e.g., the pump 52, produces electrical effects, which produce noise that can be picked up by the hydraulic line 48 and can interfere with the analysis and display of the ECG on the monitor 37.

The electrical emissions or signals are usually observed in ECG leads connected to a patient who is being transfused or infused with the electrically conductive solution. Any currents that flow in the patient's body as a result of this potential are sensed as characteristic noise added to the ECG signals.

This noise has been observed in patients connected to a peristaltic pump for cardiac assist, dialysis treatments and irrigation of an ablation catheter used in treating cardiac arrhythmias. Many sources have been proposed as sources for the noise, some focusing on the pump itself.

Without being bound by any particular theory, the following discussion is offered to facilitate understanding of the embodiments disclosed herein:

In one respect the hydraulic line 48 may function as a receiving antenna that collects noise from the surrounding environment and may constitutes one source of the noise.

In another respect, the pump may be another source of electrical noise, created by a triboelectric effect, whereby an induced charge is created on the surface of flexible tubing used in the pump and on the surface of the rotor surfaces used to compress the tubing. The rubbing or deforming action of the rotor against the tubing surface displaces electrical charge. Some of the charge is collected on the rotor and some is collected on the tubing surface. The tubing wall is generally an insulator, so that the external charge on the outside surface of the tube is induced on the inside of the tubing bore if the fluid in the tubing is an electrical conductor. In consequence, a generator potential appears between the electrically conductive fluid and the pump rotor. Any electrical circuit connecting these two points allows current to flow. Such current, if sensed or intercepted by the EKG circuitry, produces undesirable signals on the EKG tracing that are perceived as "ECG noise" by the operator. Because the triboelectric potential appears in series with the capacitance of the external and internal tubing walls, which are generally insulators (plastic), the triboelectric current has bursty characteristics.

Additionally or alternatively, The observed current may arise from a piezoelectric effect in the tubing walls.

Further additionally or alternatively, there appears to be a strong amplification mechanism resulting from the motion of the tubing walls as they are squeezed between the rotor rollers and the pump race, causing a dynamic change in tubing capacitance, which is in series with the triboelectric charge.

The noise, as observed on an ECG leads, appears as spikes, making the ECG signals difficult to interpret, and these spikes can even be confused as ECG waves themselves. Additionally, a fast Fourier transform applied to the noise to obtain its power spectrum finds component sinusoids at repetition frequencies equal to the impact rate of the rotor rollers (N) on the tubing surface along with higher harmonics. The repetition frequencies are dependent on the number of rollers in a rotor, and are to be distinguished from the rotor rotation rate itself.

First Embodiment

In one embodiment, the inventors have found that connecting an electrically conductive wire 56 between the electrolytic fluid, e.g., between the peristaltic pump effects a significant reduction in the electrical interference.

In order to minimize the number of conductors in the area of operation, the wire 56 may be incorporated in the hydraulic line 48 leading from the reservoir 46.

Figure 2:
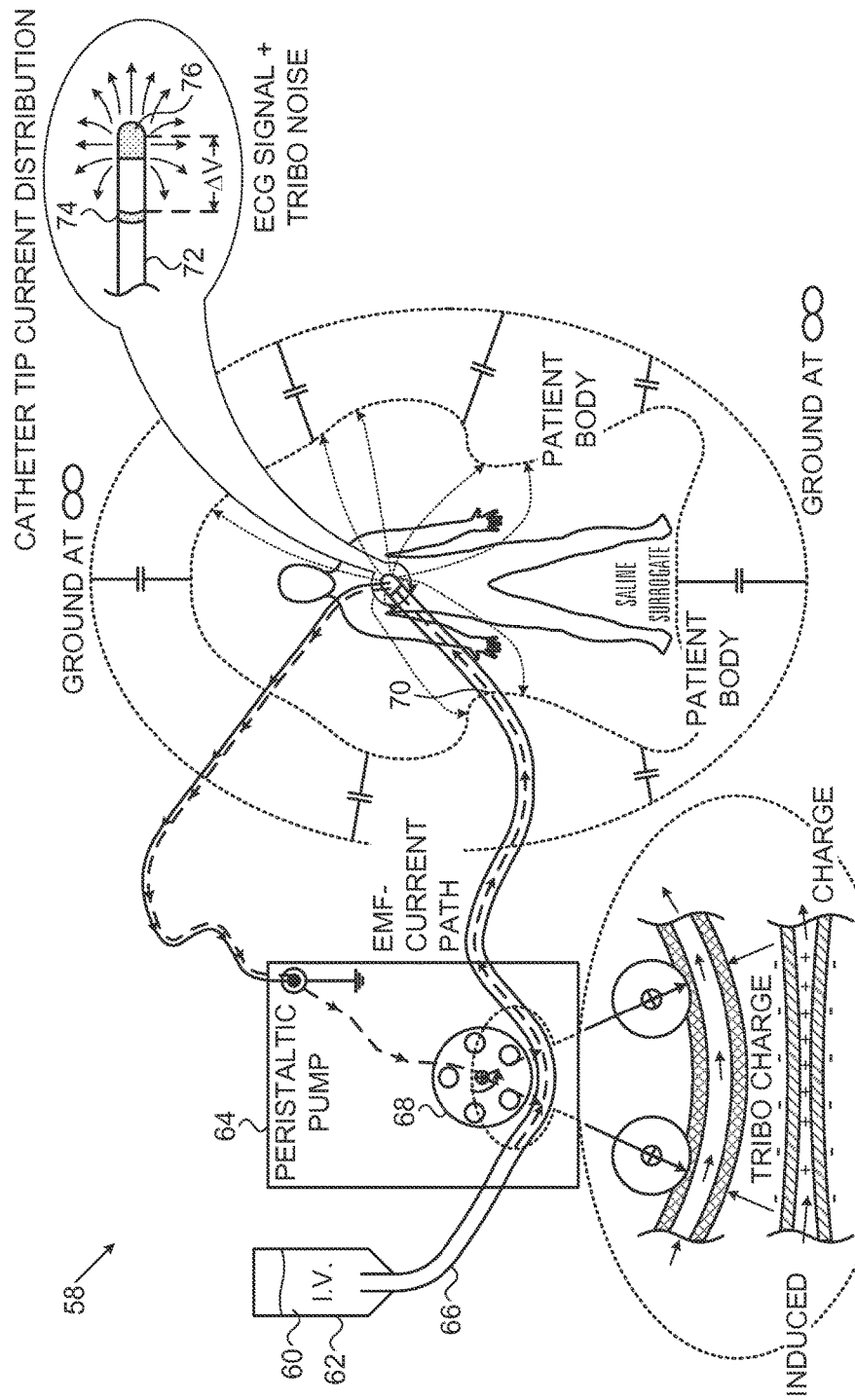
FIG. 2 is a schematic diagram of aspects of a cardiac catheterization irrigation system that illustrates electrical events that occur during operation, in accordance with an embodiment of the invention.

Reference is now made to FIG. 2, which is a schematic diagram of aspects of a cardiac catheterization irrigation system 58, and which illustrates certain electrical events that occur when the system 58 is used in medical procedures, and which are modified in according to embodiments of the invention.

In the system 58, saline 60 stored in an intravenous (I.V.) bottle or reservoir 62 is propelled by a peristaltic pump 64 through tubing 66, which is typically polyvinyl chloride (PVC) tubing. The pump 64 comprises a rotating contact 68, which typically includes a metallic rotor or race and metallic bearings, e.g., roller bearings. The fluid continues through the tubing 66, and thence through a catheter 70, terminating in its distal segment 72 where various electrodes are disposed, including sensing electrode 74, and ablation electrode 76.

A triboelectric effect occurs in parts of the system 58, particularly where the rotating contact 68 of the pump 64 compresses the tubing 66, which causes an triboelectric charge to build up in the saline 60. The charge flows through the tubing 66, propagating downstream and forming a circuit through the ablation electrode 76, and returning to the pump 64 via the patient's body as shown in FIG. 2. It is believed that the triboelectric generator in the irrigation system contributes to the spurious signals seen on the electrocardiogram. Any disturbance of the triboelectric generator or interruption or diversion of the closed loop generator current so that it does not pass through the ECG electrodes is sufficient to suppress this noise to a variable degree.

There are several ways to minimize the electrical potential that is generated between the saline and surrounding conductors and thereby mitigate the spurious signals.

1) In general, the capacitance between components may be reduced by adjusting any or all parameters in the generic capacitance equation:

$$C = e0 * eR * (\text{EffectiveArea}/\text{EffectiveSeparation}),$$

where C is capacitance; e0 is the vacuum dielectric constant; and eR is the relative dielectric constant of insulators or semi-insulators placed between the exterior boundary of the tubing and any conductors constituting a return path for the generated charge. The effective area (EffectiveArea) of those conductors is the effective electrical surface area of the components, and the effective separation (EffectiveSeparation) is the effective distance measured parallel to the electric field induced by the charge separation and perpendicular to the plane of the surface area upon which said charge resides.

Replacing metallic roller bearings and race with non-conductive equivalents, such as ceramic or polymer, reduces eR from a large number (>1000) to between 1 and 11 for common ceramic dielectrics. As an example, the race could be replaced with Delrin®, available from E. I. DuPont de Nemours & Co., Wilmington, Del. 19898. Delrin is a tough, "non-wearing" acetal homopolymer with an eR value of about 2.5. The thicker the race, then the lower the capacitance. Replacing the roller bearings with plastic or ceramic will also accomplish the same reduction in capacitance. Even replacing the cavity in which the steel rollers turn with a ceramic pocket will reduce the capacitance.

Altering the physical or chemical composition of the PVC tubing may suppress charge separation. The extrusion process that forms the tubing has the effect of orienting and aligning the PVC molecular strands. Aligned solids of this sort have piezoelectric characteristics, and can produce charge from mechanical compression. By randomizing the molecular strands through a heat treating process or adding an electrically conducting material to the PVC, the charge separation potential can be largely mitigated by preventing the physical process that creates it or by effectively shorting it out.

A generative component for the observed charge buildup could also be related to the collapse of an electric dipole layer, which forms at the interface between the saline and the plastic tubing walls when the rollers crush the walls of the tubing altering the Zeta potential. To deal with this effect, a surface treatment applied to the inside of the tubing bore could be engineered to suppress the initial formation of the dipole layer. For example, a highly symmetric chemical structure or a very long uncharged alkyl chain would effectively weaken the usual short highly polar ionic dipoles that normally form. While the dipole strength may be weakened by reducing the ionic strength or molality of the saline at the pump, this is inconvenient because it would involve complex mixing components in order to satisfy human physiologic requirements.

EXAMPLE

Figure 3:
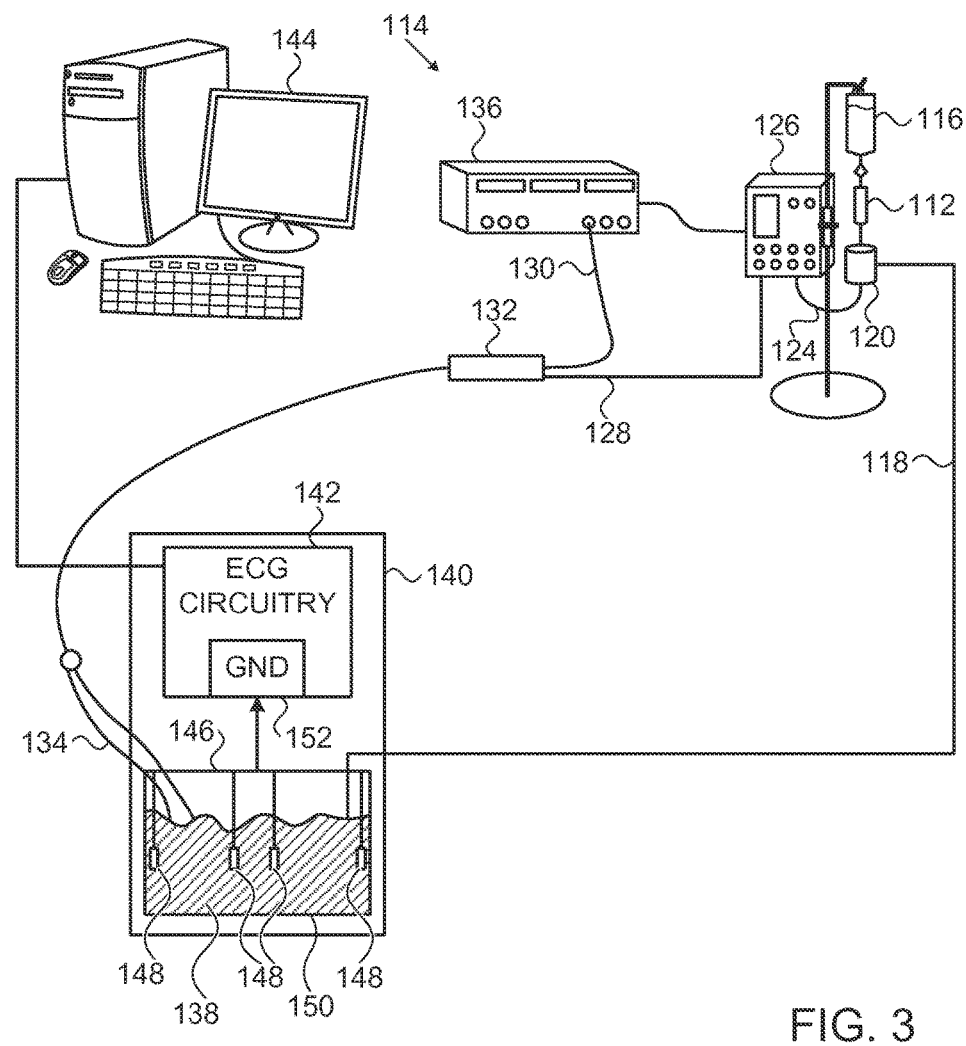
FIG. 3 is a schematic diagram of a test arrangement for measuring electrocardiogram noise reduction, in accordance with an embodiment of the invention.

Reference is now made to FIG. 3, which is a schematic diagram of a test arrangement 114 using an RF signal generator, in accordance with an embodiment of the invention. An intravenous infusion pack 116, containing saline, constitutes an electrolyte fluid reservoir, as described above. An electrical cable 118, leading from a line 124 downstream of a drip chamber 112, is connected to saline 138 in an aquarium 150. The saline flows from the drip chamber 112 through a connector 120 to reach the line 124, and is in electrical contact with the cable 118. The line 124 extends from the connector 120 to a pump 126.

Hydraulic lines 124, 128 interconnect the intravenous infusion pack 116, and the pump 126. An electrical Line 130 connects a handle 132 and a catheter 134 with an RF generator 136. The line 128 extends from the pump 126 to the handle 132 of catheter 134. The distal end of the catheter 134 is inserted into the aquarium 150 containing saline 138, which emulates a human subject.

A test system 140 includes ECG circuitry 142, which is connected to a display 144. Four ECG leads 146 are connected to the ECG circuitry 142 and to metal patches 148 that are mounted on the internal surfaces of the aquarium 150 in contact with the saline 138. The electrical cable 118 connects the intravenous infusion pack 116 to the saline 138 in the aquarium 150.

Figure 4:
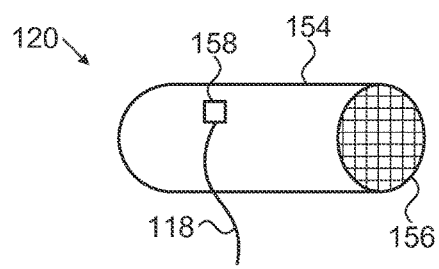
FIG. 4 is a schematic diagram of a connector for establishing electrical continuity between fluid and an electrical cable, which is constructed in accordance with an embodiment of the invention.

Reference is now made to FIG. 4, which is a schematic diagram of the connector 120 (FIG. 3), which is constructed in accordance with an embodiment of the invention. The connector 120 is tubular, having an outer metal shell 154, and a lumen filled with an electrically conductive net or sponge 156. The sponge 156 assures extensive physical contact with saline flowing in the lumen of the connector 120, and increases its conductance. An electrical connector 158 is provided on the metal shell 154 so that electrical continuity exists between the saline in the lumen, the sponge 156 and the cable 118.

Second Embodiment

Figure 5:
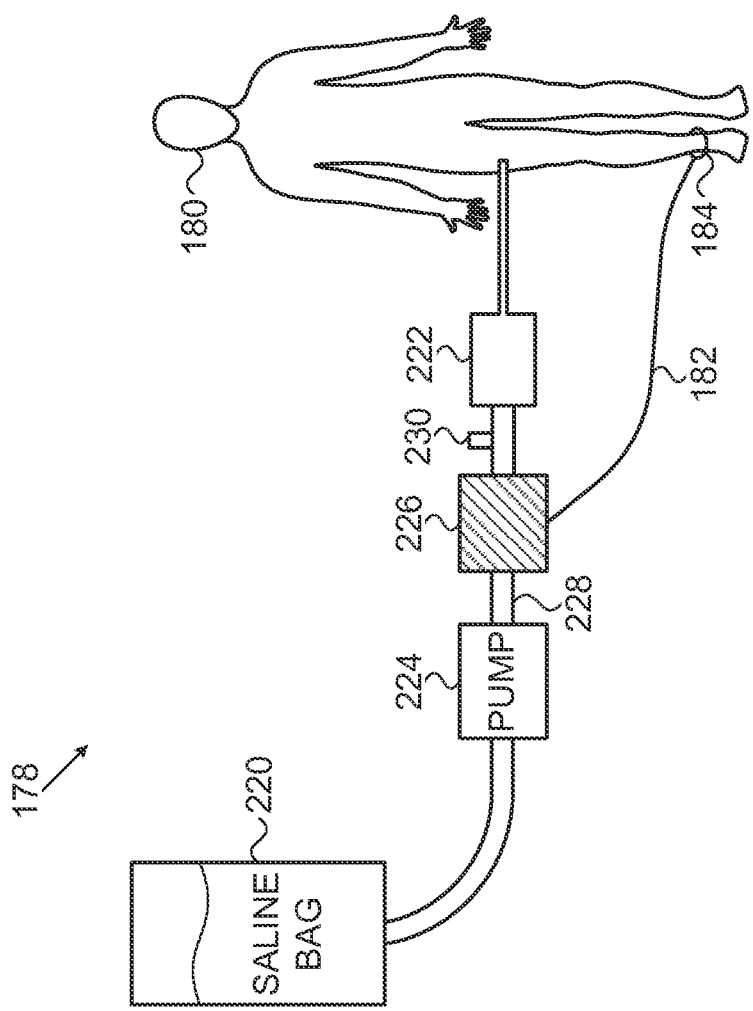
FIG. 5 is a schematic diagram of a system for reducing electrocardiogram noise, in accordance with an alternate embodiment of the invention.

Reference is now made to FIG. 5, which is a schematic of a system 178 for reducing electrocardiogram noise, in accordance with an alternate embodiment of the invention. In this embodiment electrolyte-containing fluid in a reservoir 220 is pumped into an intravascular catheter 222 by a pump 224 is electrically connected to a subject 180 by a connector 226 and an electrically conductive cable 182, for example using a body surface electrode pad or needle electrode 184 attached to a limb or other portion of the body of the subject 180, or to a patient ground. The connector 226 may have the same structure as the connector 120 (FIG. 4), The cable 182 may be shielded. The connector 226 is placed in a hydraulic line 228 or on a stopcock downstream from the reservoir 220. Preferably the connector 158 is disposed downstream of the pump 224.

Figure 6:
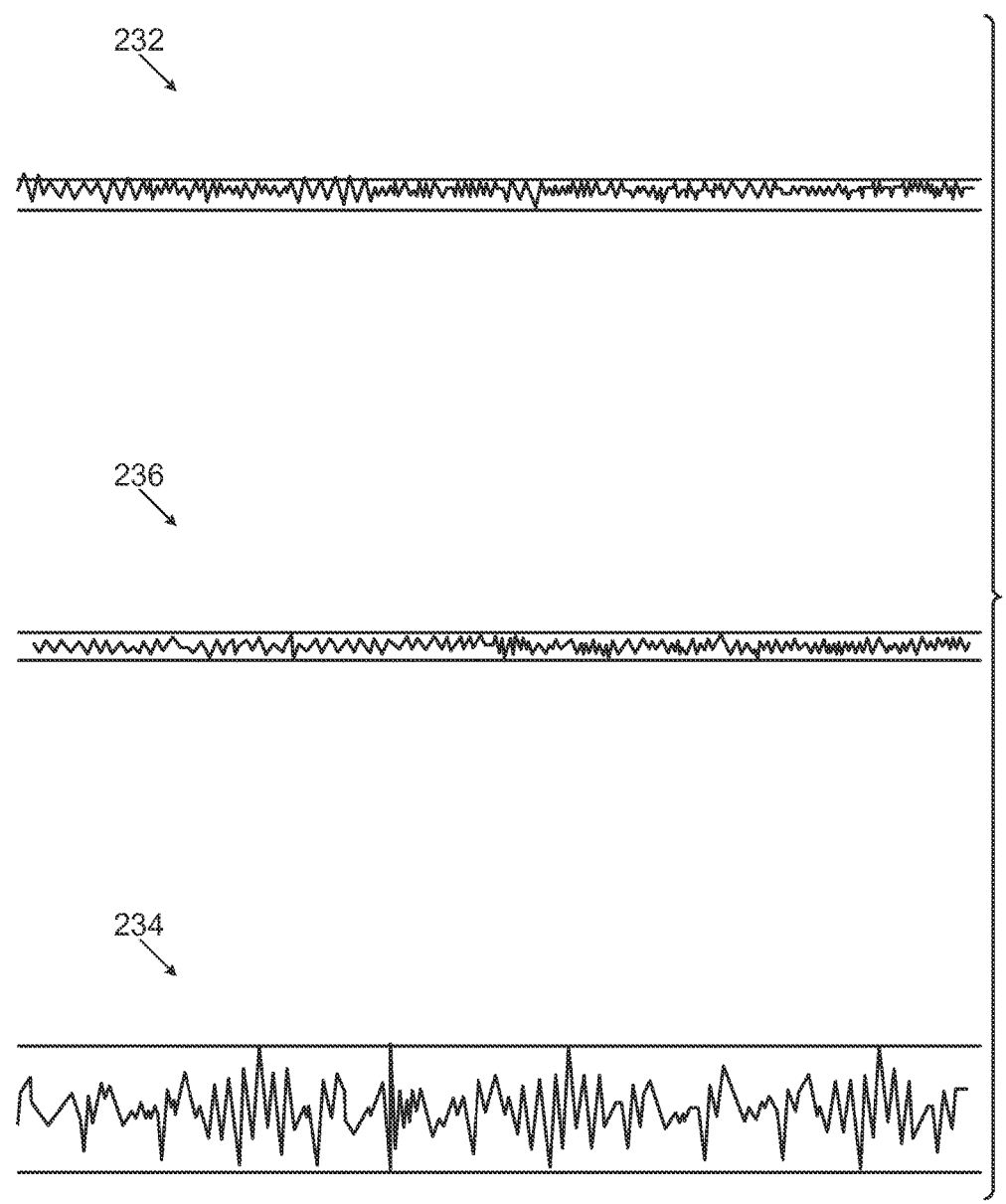
FIG. 6 shows three charts of recorded ECG data when the system shown in FIG. 5 is in operation, in accordance with an embodiment of the invention.

Reference is now made to FIG. 6, which presents recorded ECG data when the system 178 (FIG. 5) is in operation, in accordance with an embodiment of the invention. The data were recorded using the CARTO 3 system, a NaviStar® Thermo-Cool® catheter, and a SmartAblate™ pump (available from Cordis Corporation). The RF ablation generator was not active. An aquarium was used to simulate a patient, as described above with reference to FIG. 3.

ECG strip 232 is a baseline tracing, before attachment of the cable 182. Background noise is shown, with a magnitude of about 0.02 mV.

In ECG strip 234 the pump is active. Noise has increased to a value of about 0.07 mV.

In ECG strip 236 the pump remains in operation. The cable 182 has been connected thereby shorting the saline in the irrigation tubing to saline bath water. The noise level has returned to the baseline value of about 0.02 mV.

Third Embodiment

Figure 7:
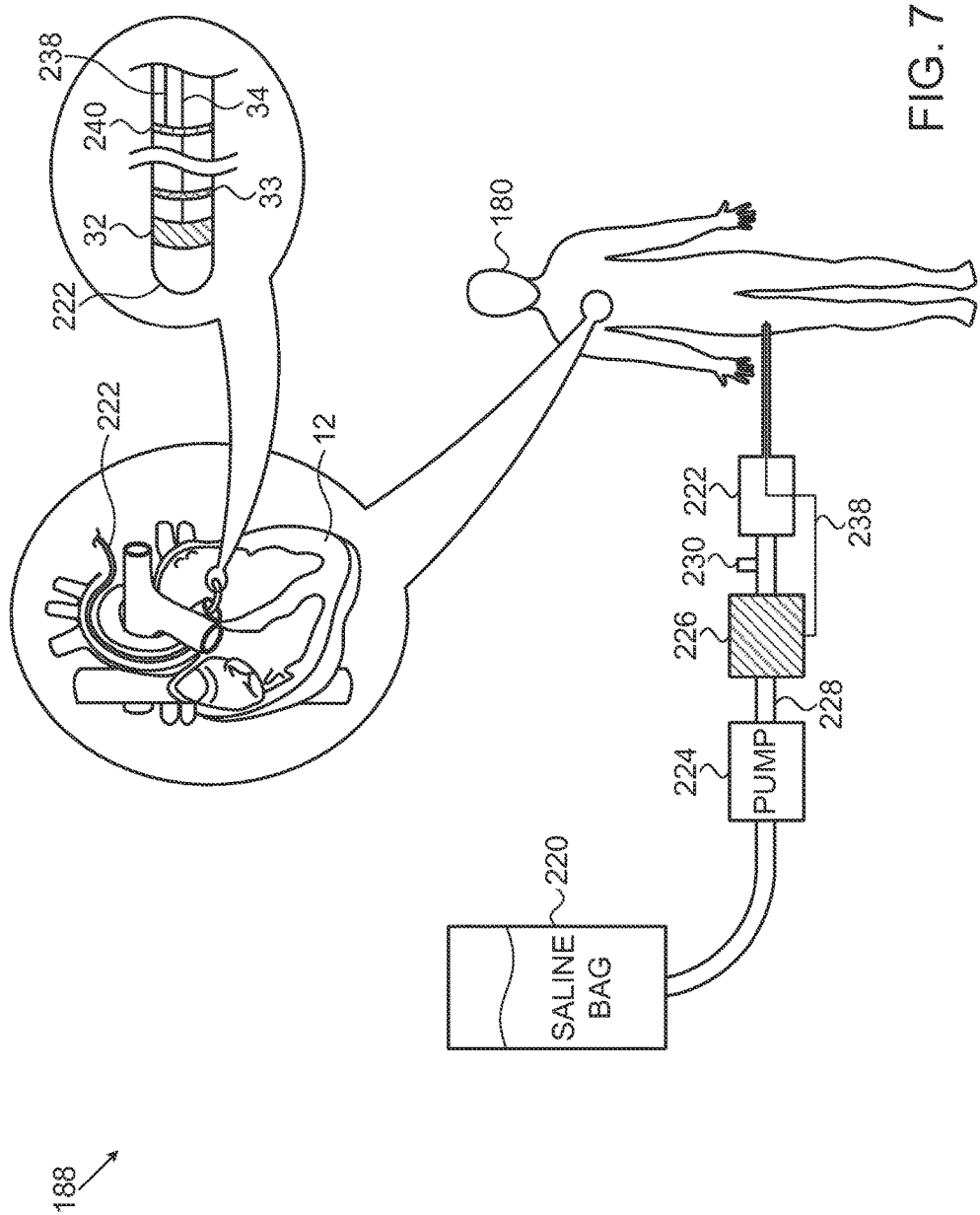
FIG. 7 is a schematic of a system for reducing electrocardiogram noise, in accordance with an alternate embodiment of the invention.

Reference is now made to FIG. 7, which is a schematic of a system 188 for reducing electrocardiogram noise, in accordance with an alternate embodiment of the invention. The arrangement in FIG. 7 is similar that of FIG. 5. However, a wire 238 now extends from the connector 226 to an electrode 240 located on the catheter 222, but proximal to electrodes 32 and 33, for example in the inferior vena cava.

Alternatively, the electrode 240 may be disposed on a second catheter (not shown), which has been introduced into the subject, for example into the vascular system or the gastrointestinal tract. The wire 238 is rerouted to the electrode 240 mutatis mutandis.

Fourth Embodiment

Figure 8:
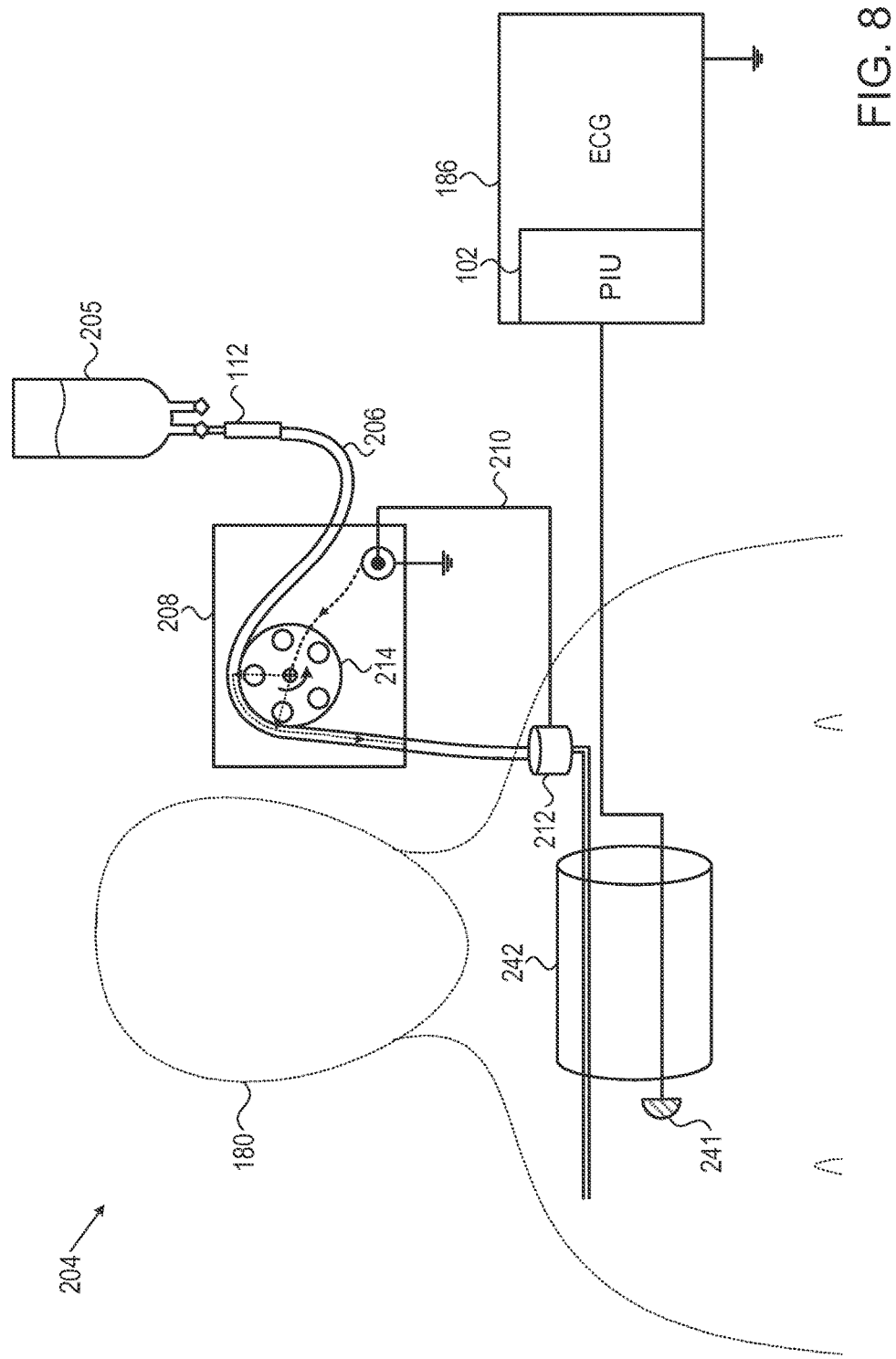
FIG. 8 is a schematic diagram of an infusion system, in accordance with an alternate embodiment of the invention.

Reference is now made to FIG. 8, which is a schematic diagram of an arrangement 204 of an infusion system, in accordance with an alternate embodiment of the invention. In this embodiment, a saline solution 205 in tubing 206 is shorted to a peristaltic pump 208 using a wire 210 that extends from a connector 212 to a metal rotor 214 or rollers in the pump 208. The wire 210 electrically connects the saline solution 205 that is propelled by the pump 208 through the tubing 206, thereby shorting out the tribogenerator. The connection may alternatively be realized by an electrically conductive nipple whose inside surface is in contact with the saline and whose body is connected to the current return side of the pump rotor. ECG data is obtained via PIU input 102 in console 186 from electrode 241 on catheter 242

The arrangement 204 has been tested using a saline surrogate for a patient tissue model similar to the test arrangement shown in FIG. 3. The irrigation peristaltic pump pushes normal saline through tubing connected to the nipple and further attached to an irrigated catheter within the patient's body. The current flowing through the saline channel in the catheter and into the patient is the source for the ECG noise signal.

Fifth Embodiment

Figure 9:
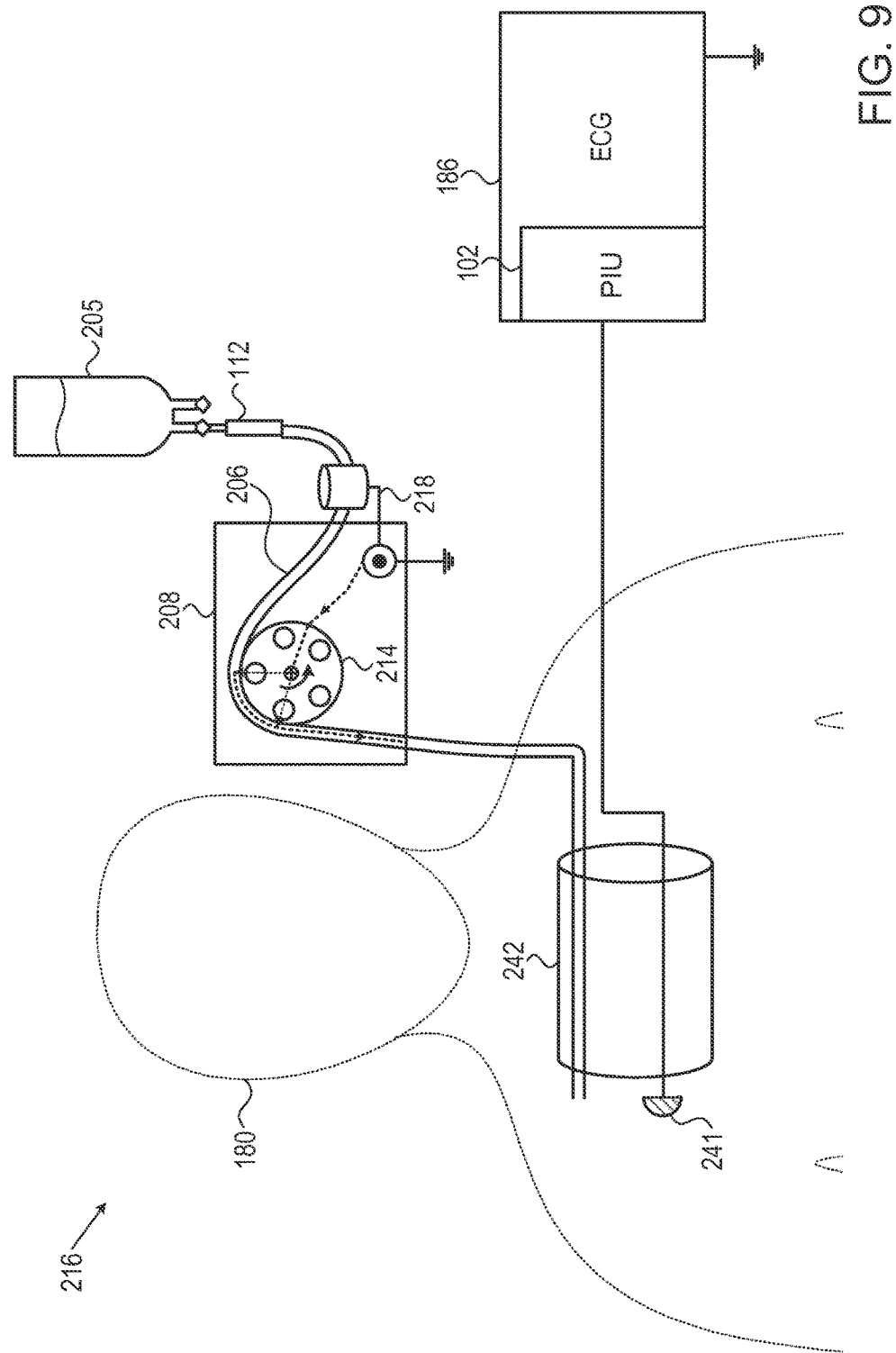
FIG. 9 is a schematic diagram of an arrangement of an infusion system, in accordance with an alternate embodiment of the invention.

Reference is now made to FIG. 9, which is a schematic diagram of an arrangement 216 of an infusion system, in accordance with an alternate embodiment of the invention. The arrangement 216 is similar to the arrangement 204 (FIG. 8). However, shorting the generator potential is accomplished by forming an electrical connection between the pump 208 and the drip chamber 112 or other fluid source feeding the input side of the pump by a wire 218 or by a conductive nipple. By shorting the saline in tubing 206 to the rotor or pump frame, the generator potential is effectively short circuited on the input side of the pump 208 rather than on the output side as in the previous embodiment.

Sixth Embodiment

Referring again to FIG. 9, the embodiments described above can be further modified by mitigating the surface charge of the tubing. One way to accomplish this is by coating the outer surface of the tubing or hydraulic line with any material containing liquid water and an ionic surfactant that renders the water slightly electrically conductive and the tubing surface hydrophilic. Coating may be accomplished by squirting, spraying, or rubbing saline, hand soap or electrode gel on the outside of the tubing. While the foregoing description applies to a very broad class of substances, it has been found that certain materials were particularly effective in disrupting the triboelectric generator, namely ordinary hand soap, saline, and electrode gel.

Non-conductors such as lubricating oil were also tested in an attempt to disrupt the surface of the triboelectric generator. These altered the potential depending on how dry or poorly conductive the oil. Dry or poorly conductive oil was less effective than oil mixed with water or having conductive properties. Oil mixed with three-micron aluminum flakes constitute a very effective disrupting agent, but do not completely suppress the potential, because the conduction mechanism appears to be capacitive coupling between aluminum particles, rather than ionic conductivity as in water. As soon as the water in any of these preparations evaporates, the triboelectric generator returns to its original potential, reinstituting electrical noise.

Alternatively, the outer surface of the tubing may be coated with an electrical conductor, so that mechanical contact with the metallic rotor 214 is essentially metal-onmetal. Indium tin oxide is suggested. Wrapping the tubing in aluminum foil so that the contact point is metallic roller on foil completely eliminates triboelectric charging.

Alternatively, impregnating the plastic material of the tubing with anti-static chemical additives, e.g., metal particles, so that the tubing walls are slightly conductive, shorts out the triboelectric generator. These chemical additives tend to be hydrophilic attracting water molecules to bind with the plastic surface or volume so that it is slightly electrically conductive.

Further alternatively, adding "anti-static" chemical additives to the outer surface of the tubing is also effective.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A catheterization system, comprising:
   a flexible catheter adapted for insertion into a heart of a living subject, having a distal portion and a lumen for passing an electrically conductive fluid therethrough to exit the catheter at the distal portion;
   a fluid reservoir connected by a hydraulic line to the lumen for supplying the electrically conductive fluid to the catheter;
   a pump for propelling the electrically conductive fluid to the lumen of the catheter, the pump having a frame and a rotating element that acts upon the hydraulic line; and
   an electrically conductive cable forming an electrical connection between the electrically conductive fluid in the hydraulic line and the rotating element.

2. The system according to claim 1, wherein the rotating element is metallic.

3. The system according to claim 1, wherein the rotating element is formed from a ceramic.

4. The system according to claim 1, wherein the rotating element is formed from a polymer.

5. The system according to claim 1, wherein the rotating element is formed from an acetal homopolymer.

6. The system according to claim 1, wherein the electrically conductive cable connects to the frame of the pump.

7. The system according to claim 1, wherein the electrically conductive cable connects to the rotating element of the pump.

8. The system according to claim 1, wherein the rotating element is electrically non-conductive.

9. The system according to claim 1, wherein the electrical connection with the electrically conductive fluid is downstream from the pump.

10. The system according to claim 1, wherein the electrical connection with the electrically conductive fluid is upstream from the pump.

11. The system according to claim 1, wherein a portion of an outer surface of the hydraulic line is coated with an antistatic chemical, the portion contacting the outer surface with the rotating element of the pump.

12. The system according to claim 1, wherein a portion of an outer surface of the hydraulic line is coated with an antistatic chemical selected from the group consisting of soap water, saline and water, the portion contacting the outer surface with the rotating element of the pump.

13. The system according to claim 1, wherein a portion of an outer surface of the hydraulic line is coated with an electrical conductor, the portion contacting the outer surface with the rotating element of the pump.

14. A method for monitoring electrical activity, comprising the steps of:
    connecting a reservoir of an electrically conductive fluid to a peristaltic pump, the peristaltic pump having a rotating element and a frame, wherein the peristaltic pump exerts a force on a hydraulic line to cause the electrically conductive fluid to flow through the hydraulic line;
    connecting electrocardiogram circuitry to a subject;
    forming an electrical connection with an electrically conductive cable between the electrically conductive fluid in the hydraulic line and the rotating element;
    operating the peristaltic pump to cause the electrically conductive fluid to flow from the reservoir into the subject; and
    while operating the peristaltic pump, monitoring electrical activity in a heart of the subject with the electrocardiogram circuitry.

15. The method according to claim 14, wherein the electrical connection is formed with the frame of the peristaltic pump.

16. The method according to claim 14, wherein the electrical connection is formed with the rotating element of the peristaltic pump.

17. The method according to claim 14, wherein the rotating element is metallic.

18. The method according to claim 14, wherein the rotating element is electrically non-conductive.

19. The method according to claim 14, wherein a portion of the hydraulic line is coated with an electrical conductor, further comprising contacting the portion with the rotating element.

20. The method according to claim 19, wherein the electrical conductor is indium tin oxide.

21. The method according to claim 19, wherein the electrical conductor is aluminum foil.

22. The method according to claim 14, wherein the hydraulic line is impregnated with an anti-static chemical.

23. The method according to claim 14, wherein an outer surface of a portion of the hydraulic line is coated with a material containing liquid water and an ionic surfactant, further comprising contacting the portion with the rotating element.

24. The method according to claim 23, wherein the material is selected from the group consisting of hand soap, saline, an oil-water mixture, and electrode gel.

25. The method according to claim 14, wherein a portion of the hydraulic line is impregnated with an anti-static chemical, further comprising contacting the portion with the rotating element.

26. The method according to claim 14, wherein a portion of an outer surface of the hydraulic line is coated with an anti-static chemical, further comprising contacting the portion with the rotating element.

* * * * *